United States Patent [19]

Rochon et al.

[11] Patent Number: 4,533,502

[45] Date of Patent: Aug. 6, 1985

[54] PLATINUM (II) COMPOUNDS AND THEIR PREPARATION

[76] Inventors: Fernande D. Rochon; Pi-Chang Kong, both of C.P. 8888, Succ. A, Montréal, Canada, H3C 3P8

[21] Appl. No.: 468,619

[22] Filed: Feb. 22, 1983

[51] Int. Cl.³ ............................................... C07F 15/00
[52] U.S. Cl. .................................. 546/8; 514/492; 556/136; 556/137; 546/9
[58] Field of Search ................................ 260/429 R

[56] References Cited

U.S. PATENT DOCUMENTS

| | | | |
|---|---|---|---|
| 3,892,790 | 7/1975 | Tobe et al. | 260/429 R |
| 3,904,662 | 9/1974 | Tobe et al. | 260/429 R |
| 4,115,418 | 9/1978 | Gale et al | 260/429 R |
| 4,119,653 | 10/1978 | Tobe et al. | 260/429 R |
| 4,119,654 | 10/1978 | Tobe et al. | 260/429 R |
| 4,140,707 | 2/1979 | Cleare et al. | 260/429 R |
| 4,182,724 | 1/1980 | Tobe et al. | 260/429 R |
| 4,200,583 | 4/1980 | Kidani et al. | 260/345.7 |
| 4,203,912 | 5/1980 | Hydes et al. | 260/429 R |
| 4,225,529 | 9/1980 | Hydes et al. | 260/429 R |
| 4,230,631 | 10/1980 | Hydes et al. | 260/429 R |
| 4,250,189 | 2/1981 | Hydes et al. | 260/429 R |
| 4,329,299 | 5/1982 | Hydes | 260/429 R |

FOREIGN PATENT DOCUMENTS 2060615  5/1981  United Kingdom .

OTHER PUBLICATIONS

Cleare et al., *Bioinorganic Chemistry*, 2: (1973) 187–210.
Chatt, *J. Chem. Soc.*, (1951) 652–658.
Braddock et al., *Inorganic Chemistry*, 13: (1974) 1170–1175.
Rochon et al., *Journal of Clinical Hematology and Oncology*, vol. 12, 39–43 (1982).
Courtat et al., *J. Organometallic Chem.*, 145: (1978) 343–357.
Braddock et al., *Chem-Biol. Interactions*, 11: (1975) 145–161.
Chatt et al., *J. Chem. Soc.*, (1955) 2787–2793, 3658–3664.
Dhara, *Indian J. Chem.*, 8: (1970) 193–194.
Cleare et al., *Platinum Met. Rev.*, 17: (1973) 2–13.
Kukushkin and Dkhara, *Russian Journal of Inorganic Chemistry*, 15 (2):(1970) 304–305.
Kukushkin, Karpeiskaya and Trofimov, *Russian Journal of Inorganic Chemistry*, 16 (3):(1971) 408–410.
Kong and Rochon, *Can. J. Chem.*, 57: (1979) 682–684.
Kong and Rochon, *Can. J. Chem.*, 56: (1978) 441–445.
Rochon, Kong and Melanson, *Can. J. Chem.*, 59: (1981) 195–198.
Lock and Zvagulus, *Inorg. Chem.*, 20: (1981) 1817–1823.
Rochon, Kong and Melanson, C. J. Chem., 58, 97–101 (1980).
Rochon and Melanson, *Acta Cryst.* B37, 690–692 (1981).

*Primary Examiner*—Helen M. S. Sneed

[57] ABSTRACT

This invention relates in one aspect to various methods for preparing platinum (II) complexes and in another aspect to certain novel ligand platinum complexes, i.e.:

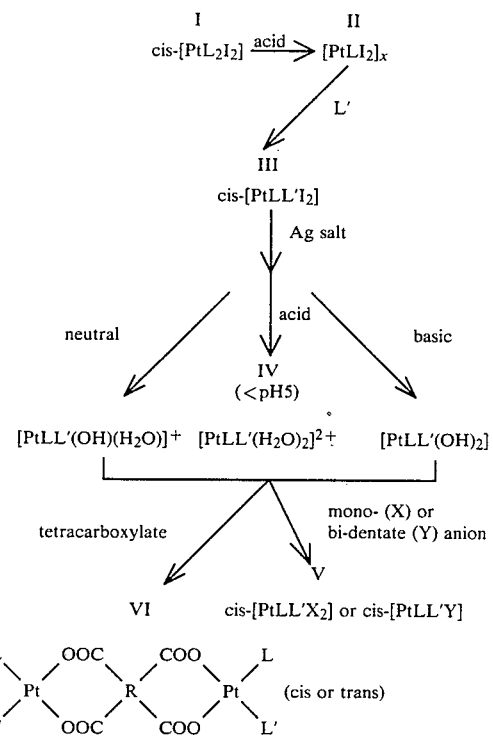

where X is a monodentate ligand ($X_2$) or a bidentate ligand Y, and where L and L' are ligands bonded through amine nitrogen (including pyridine type nitrogen), or DMF, and where preferably $L \neq L'$.

Various novel platinum compounds within the above reaction series are also claimed.

10 Claims, No Drawings

PLATINUM (II) COMPOUNDS AND THEIR PREPARATION

BACKGROUND OF THE INVENTION

Courtat et al., *J. Organometallic Chem.*, 145: (1978) 343–357, teach the opening of chlorine-bridged dimers of the formula [Pt(II)LCl$_2$], where L is pyridine, piperidine, p-methoxyaniline, methyl-2-pyridine, methyl-4-pyridine, and trimethyl-2,4,6-pyridine with ligands such as olefins, nitriles, dimethylsulfoxide, dimethylsulfide, dimethylformamide, as well as by the use of vinyl-4-pyridine and allyl amine to provide both cis and trans compounds. There is no teaching of iodo compounds.

Braddock et al., *Chem-Biol. Interactions*, 11: (1975) 145–161, teach inter alia mixed ligands of the cis-[PtLL'Cl$_2$] type where the mixed ligands are ammonia, paired with ethyleneimine, ethylamine, cyclopentylamine, and dimethylsulfoxide, as well as cyclohexylamine paired with dimethylsulfoxide and dimethylsulfide.

Chatt et al., *J. Chem. Soc.*, (1955) 2787–93, describe methods for preparing binuclear platinum chloride complexes of the type [L$_2$Pt$_2$Cl$_4$]. The reference teaches the sometime formation of [Pt$_2$LL'Cl$_2$] from the dimer. The preparation of one iodine bridged complex was reported, but the ligand is apparently not amine.

Chatt et al., *J. Chem. Soc.*, (1955) 3858–64 describe the reaction of amines with the bridged dimers [Pt$_2$LX$_2$]$_2$ where the halogen is usually chlorine. The preparation of the mixed ligand compounds trans-[Pt(tripropylphosphine)(NH$_3$)I$_2$] and trans-[Pt(tripropylphosphine)(piperidine)I$_2$] are reported, apparently prepared by reacting the corresponding dichloride in acetone with potassium iodide and then an amine. The reaction is reported as difficult, with the apparent formation of [pt(tripropylphosphine)I$_2$]$_2$.

Dhara, *Indian J. Chem.* 8: (1970) 193–4, describes the preparation of cis-[PtL$_2$I$_2$] which method is the method of choice for preparing the starting compounds employed in this invention.

Cleare et al., *Platinum Met. Rev.*, 17: (1973) 2–13 describe Dhara's reaction (supra) as a general method for preparing cis-[PtL$_2$I$_2$] and teach that these compounds react with silver nitrate and an appropriate anion to produce other cis-[PtL$_2$X$_2$] or [PtL$_2$Y] species which X is a monodentate ligand and Y is a bidentate ligand. The reference does not discuss compounds where L$\neq$L'.

Cleare et al., *Bioinorganic Chemistry*, 2: (1973) 187–210, describe various platinum II complexes and confirm that the method of Dhara (supra) is general to provide cis-[PtL$_2$I$_2$]. No species where L$\neq$L' are discussed.

Chatt, *J. Chem. Soc.*, (1951) 652–658, describes halogen-bridged Pt compounds where the ligand is coordinated through P, As and Sb.

Braddock et al., *Inorganic Chemistry*, 13: (1974) 1170–1175 describe cis-[Pt(amine)(DMSO)Cl$_2$] complexes.

U.K. patent application No. 2,060,615 is directed to platinum compounds which encompass cis-[Pt(aliphatic amine)(NH$_3$)(halogen)$_2$]. Only chloro compounds are specifically taught, with very low yields (less than 10%).

U.S. Pat. No. 4,119,653 and U.S. Pat. No. 4,182,724 inter alia teach cis-[Pt(n-propylamine)$_2$I$_2$] and reaction with AgNO$_3$ with conversion to the Cl$_2$ species. The reference encompasses dissimilar amine ligands but does not teach their preparation.

U.S. Pat. No. 4,225,529 inter alia encompasses dissimilar amine ligands; and specifically describes cis-[Pt(amine)$_2$I$_2$] compounds and their reaction with AgNO$_3$ to replace I$_2$ with other ligands.

U.S. Pat. No. 3,892,790 inter alia encompasses dissimilar amine ligands; and specifically describes cis-[Pt(alicyclic amine)$_2$Cl$_2$] compounds.

The following patents also show various Pt(II) amine ligand complexes: U.S. Pat. Nos. 4,200,583; 4,140,707; 4,119,654; 4,115,418; 3,904,663; and 4,230,631.

It is noted that several of the above references discuss the antitumor effects of various platinum complexes and significant evaluation of various platinum compounds as antitumor agents is ongoing in the art.

Various Pt(II) complexes have been shown in the art to have antitumor activity. While various cis-[PtLL'X$_2$] compounds, where L$\neq$L', have been broadly or generically taught, or even claimed in the patent art, very few of these compounds have been prepared, and the art related to those few preparations show low yields and/or mixed isomer products. Many of the references which generically encompass the mixed ligand compounds give no method for their preparation.

The preparation of mixed ligands cis-PtII complexes is desirable to evaluate these compounds as to their biological activity. It has now been found that cis-PtII complexes, preferably having mixed ligands, can be prepared through reaction of an oligomer, [PtLI$_2$]$_x$, in a manner such that the cis-ligand compound cis-[PtLL'I$_2$] is formed in high yield with no trans-isomer formation.

DESCRIPTION OF THE INVENTION

This invention relates in one aspect to various methods for preparing platinum (II) complexes and in another aspect to certain novel ligand platinum complexes, i.e.:

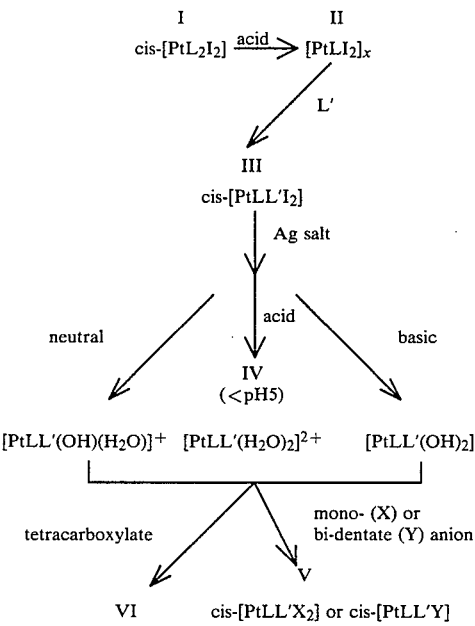

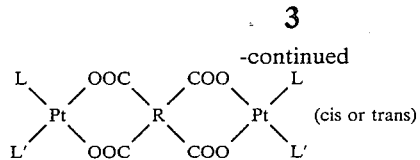

where X is a monodentate ligand ($X_2$) or a bidentate ligand Y, and where L and L' are ligands bonded through amine nitrogen (including pyridine type nitrogen), or DMF, and where preferably $L \neq L'$.

The starting cis-$[PtL_2I_2]$ and the resultant oligomer $[PtLI_2]_x$ comprise those compounds wherein L is an amine coordinated to the Pt through its N atom such that the platinum is present as $Pt^{2+}$, as well as DMF (coordinated through its O atom). Useful amines include primary and secondary monoamines and pyridine-type nitrogen containing compounds, i.e. compounds containing a pyridine type nitrogen

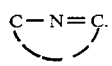

Useful amine ligands include ammonia (ammine), branched and straight chain lower alkyl amines (e.g. methyl, ethyl, n-propyl, isopropyl, n-butyl, n-octyl, isooctyl); aryl amines (e.g. phenyl, lower alkyl-, lower alkenyl halo-, nitro-, lower alkoxysubstituted phenyl and naphthyl), aralkylamines, (e.g. phenylmethyl, 2-napthyl-1-ethyl); lower alkenyl (e.g. alkyl, 4 amino-1-butene); cycloalkyl (e.g. cyclopropyl through cycloheptyl); cycloalkylenyl (e.g. 2-cyclopenten-1-yl, 2-cyclohexen-1-yl); polycyclic hydrocarbon amines (e.g. 1F adamantane-(1 or 2), endo or exo boraine); heterocyclic N-H amines (e.g. pyrrole, ethylenimine, azepine, indole, carbazole); nucleosides, nucleotides, and pyridine-type nitrogen containing compounds (e.g. pyridine, pyrazine, pyrimidine, acridine, quinoline and isoquinoline). Preferably L is other than $NH_3$. Generally, amines with saturated or unsaturated hydrocarbon, halo, nitro, lower alkoxyl and hydroxy substituents can be employed.

The starting material (I) employed in this invention and methods for its preparation useful for all the starting materials contemplated herein are taught in the art; see for example, Dhara, *Indian J. Chem.*, 8: 193–4 (1970). For example, $K_2[PtCl_4]$ is reacted with KI and an amine or ammonium hydroxide to provide cis-$[PtL_2I_2]$ where L is a ligand bonded through amine nitrogen.

In the method of the invention cis-$[PtL_2I_2]$ is converted into an iodine bridged oligomer having the repeating unit $[PtLI_2]$ by reacting the starting material with aqueous acid in a water miscible, inert solution for the starting material. Both the acid and solvent are selected to be non-reactive with the platinum under the reaction conditions. Useful solvents include water, lower alkanols, for example, methanol, ethanol, propanol, isopropanol, butanol, isobutanol and the like, acetone and tetrahydrofuran.

The present preferred acid is perchloric acid ($HClO_4$); however, acids such as $HBF_4$, $HPF_6$, $CF_3SO_3H$ or other aqueous acid can be employed.

The acid is employed in at least about a molar amount based upon the platinum present. Preferably, the acid is employed in a molar ratio of about 2 to about 5, based on platinum. Larger amounts of acid, for example, 10:1 molar amounts, can be employed, but are not necessary.

Typically, the reaction can be conducted at room temperature. If the reaction is slow, slightly elevated temperatures, for example, up to about 80° C., can be employed. The reaction temperature is not unduly critical, so long as the temperature employed does not cause significant decomposition of the oligomer product.

The resultant iodo-oligomer is very insoluble and precipitates as a colored solid which can readily be isolated, for example, by filtration and washing with water.

The oligomer can be represented by the emperical formula $[PtLI_2]_x$ where x is a lower integer 2 or higher, preferably 2 to 4. The dimer is represented by the formula

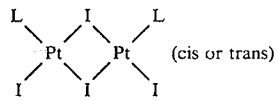

The trimer can be represented by the formula

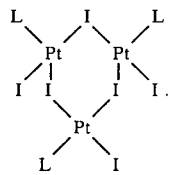

In the process of the invention, the resultant $[PtLI_2]_x$ above, is reacted with an amine to form cis-$[PtLL'I_2]$ wherein $L \neq L'$. This reaction is conducted in a manner such that the product cis-$[PtLL'I_2]$ is insoluble in the reaction medium to prevent significant isomerization of the cis-form of the product to the trans isomer. The reaction proceeds essentially quantitatively at room temperature, or even below room temperature, over time. If desired, to enhance reaction rates slightly, elevated temperatures may be useful. While the reaction temperature is not unduly critical, the temperature is generally not elevated above that temperature necessary to achieve a reasonable reaction rate, as product solubility and thus the potential for partial isomerization increases with increasing temperature.

The L' contributing amine is reacted with $[PtLI_2]$ oligomer in approximately molar amounts based on platinum, to avoid formation of a $[PtL'_2I_9]$ or $[PtLL'_2I]$ product.

The starting oligomer $[PtLI_2]_x$ is suspended in an aqueous solution of the amine reactant, preferably with stirring. Typically, the color of the starting material is deeper and more intense than that of the product cis-$[PtLL'I_2]$, thus, the reaction course can usually be monitored by color change. The reaction medium of choice is water, if desired, minor amounts of other solvents—preferably water miscible solvents—can be employed in conjunction with water, provided that the reaction product is essentially insoluble in the resultant aqueous reaction medium.

The amine employed can be any of the above enumerated amines (L) provided that $L \neq L'$. Where one of the ligands is ammine ($NH_3$) it is highly preferred that the ammine ligand is formed by using ammonia (e.g. ammonium hydroxide) to disassociate the oligomer, as it has been found the reaction procedures are more orderly when L in the oligomer is other than ammine.

In addition to the use of an amine, if desired, DMF can be employed in the same manner to contribute the L' ligand.

The resultant [PtLL'I$_2$] complex can be converted into an aqueous species IV, supra, by reaction with a silver salt in aqueous media, for example, silver nitrate or silver perchlorate, to precipitate the silver iodide. The amount of silver salt is not unduly critical, except that to remove all the iodo ion from the complex, at least a molar equivalent of silver for each mole of iodine is required. Excess silver beyond that necessary to remove the iodine merely contaminates subsequent products, if not removed. The reaction usually proceeds well at room temperature, or at most, by the use of slightly elevated temperatures. Depending on the pH of the aqueous media, the diaquo species can be written with three representative formulas IV, supra.

The aqueous species represented in the formulas are not isolated and may in fact be more complex than represented, at least in some instances, but their nature and reactivity from a reaction standpoint are apparently identical to the species having two identical L ligands which are already known in the art.

The resultant solution containing the aqueous species, after quantitative precipitation of silver iodide, is reacted with a soluble salt, e.g. alkali metal or alkaline earth metal, preferably sodium or potassium, or acid (e.g. nitric acid) of an anion sought to be added as a ligand. Where the anion is monofunctional with Pt under the reaction conditions, a significant excess of the anion can be added to assure complete reaction. Generally, while equivalent amounts can be employed, typically where both X ligands are desired to be added, at least double the equivalent amount of anion is employed. Where the anion is a polydentate anion, it may be necessary to employ equivalent ratios of Pt and anion to promote polydentate ligand formation. While reaction temperature is not unduly critical, the reaction is preferably conducted at the lowest temperature at which the reaction proceeds at a reasonable rate so as to promote precipitation of the product to drive the reaction to completion and to avoid product solubility which could result in isomerization to the trans-isomer.

Ligand (X) contributing anions which can be employed include Cl$^-$, Br$^-$, mono-carboxylate ions, NO$_3$$^-$, SO$_4$$^{--}$, PO$_4$$^{---}$, HPO$_4$$^{--}$, H$_2$PO$_4$$^-$. Polydentate contributing anions include bidentate and tetradentate polycarboxylic acids, i.e. dicarboxylates and tetracarboxylates.

Where a monodentate ligand contributing compound is reacted with the aqueous species IV, the resultant complex comprises cis-[PtLL'X$_2$] where L and L' are defined as above, and where X is Cl$^-$, Br$^-$, NO$_3$$^-$, SO$_4$$^{--}$, PO$_4$$^{---}$, HPO$_4$$^{--}$, H$_2$PO$_4$$^-$, H$_2$O or carboxylate or mixtures thereof. The general concept of converting the aqueous species IV into X$_2$ monodentate ligands containing platinous complexes by the addition of ligand contributing salts or acids is well known in the art.

Where a bidentate ligand contributing salt is reacted with the aqueous species IV, the resultant complex comprises cis-[PtLL'(Y)] where Y is for example, a dicarboxylate.

Particular examples of carboxylate ligands are monodentate carboxylato corresponding to the formula C$_N$R$_{2N+1}$COO$^-$ where N is 1-9 and R is independently hydrogen alkyl, aryl, alkaryl, aralkyl, alkenyl, cycloalkyl, cycloalkylene, halogen, hydroxyl, nitro, alkoxyl or aryloxy; and bidentate dicarboxylato such as oxalate, succinato, glutarato, pemelato, malonato, phthalato, 1,1(or 1,2-)-cycloalkyldicarboxylato or similar acid unsubstituted or with substituents as R above.

Where a tetracarboxylate is employed with the aqueous species IV, the resultant complex comprises:

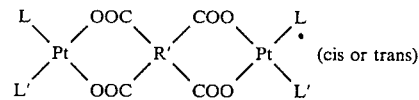

where R'—(COO)$^-$$_4$, is a tetracarboxylate, for example, a benzene, cyclobutane, or cyclopentane tetracarboxylate and where L and L' can be the same or different and are defined as above. Where L and L' are the same, the starting aqueous species IV can be formed from any cis-[PtL$_2$(halogen)$_2$] precursor such as those known in the art.

In a specific embodiment where the anion associated with silver in the silver salt is a ligand forming anion, it is sometimes possible to conduct the iodine removal step and the ligand addition step without prior separation of the silver iodide. This is especially true where additional appropriate anion is supplied to the reaction mixture from a separate soluble salt source. In this process variation, the silver salt precipitate is removed and the filtrate dried to yield the desired product.

PREFERRED GENERAL PROCEDURE

Two milimoles of cis-[PtL$_2$I$_2$] is first mixed with 10 ml of perchloric acid (0.67M). Then 30 ml of ethanol is added to the mixture which is left at room temperature for 4-6 hours. When L=pyridine, slight heating (~50° C.) is necessary. The precipitate (usually red) which is the oligomer [PtLI$_2$] is filtered off and washed with 20 ml of a 1:1 mixture of ethanol and water.

The oligomer is mixed with an excess (usually 1.5-2.5×) of L' ligand contributor (e.g. 4 ml of 1M ammonium hydroxide and 25 ml of water). The mixture is left at room temperature for about six hours. The color of the resultant mixture is usually bright yellow. The precipitate cis-[PtLL'I$_2$] is filtered and washed with water.

The product, cis-[PtLL'I$_2$] is dried at room temperature in a dessicator. It is then added to 20 ml of water. Silver nitrate is added to the mixture in a Pt:AgNO$_3$ proportion of 1:2. The silver iodide precipitate is filtered off, to yield a filtrate containing IV (supra) depending on pH.

cis-[PtLL'Cl$_2$]

The dichloride is prepared by adding a concentrated solution of KCl in excess to the above filtrate. The precipitate cis-[PtLL'Cl$_2$] is filtered off and washed with water.

cis-[PtLL (RCOO)$_2$] or cis-[PtLL R-(COO)$_2$]
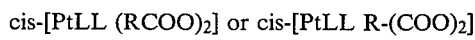

An aqueous solution of R-COO$^\ominus$ or R-(COO$^\ominus$)$_2$, e.g. as the sodium salt, is added to the above filtrate, the precipitate, cis-[PtLL'(RCOO)$_2$] or cis-[PtLL R-(COO)$_2$] is filtered off and washed with water.

EXAMPLES 1-5

In accordance with the first step of the preferred general procedure, the following oligomers were made and characterized:

| Example No. | | C | H | N | I | Pt | |
|---|---|---|---|---|---|---|---|
| 1 | [Pt(NH$_3$)I$_2$]$_x$ | — | — | 3.00 | 54.51 | 41.85 | (cal.) |
|   |   |      |      | 2.97 | 54.13 | 41.78 | (found) |
| 2 | [Pt(NH$_2$CH$_3$)I$_2$]$_x$ | 2.50 | 1.04 | — | 52.92 | | (cal.) |
|   |   | 2.81 | 1.13 | — | 53.33 | | (found) |
|   |   | 2.48 | 0.86 | — | — | | |
|   |   | 2.96 | 1.14 | — | — | | |
| 3 | [Pt(NH$_2$C$_2$H$_5$)I$_2$]$_x$ | 4.86 | 1.42 | — | 51.42 | | (cal.) |
|   |   | 4.90 | 1.46 | — | 51.52 | | (found) |
|   |   | 4.91 | 1.34 | — | — | | |
| 4 | [Pt(NH$_2$CH(CH$_3$)$_2$)I$_2$]$_x$ | 7.09 | 1.77 | — | 50.00 | | (cal.) |
|   |   | 7.53 | 1.79 | — | 49.62 | | (found) |
| 5 | [Pt(cyclopentylamine)I$_2$]$_x$ | 12.24 | 2.06 | — | 47.57 | | (cal.) |
|   |   | 12.81 | 1.88 | — | 47.48 | | (found) |

EXAMPLE 6

Preparation of cis-[Pt(cyclopropylamine)(NH$_3$)I$_2$]

Two mm of cis-[Pt(cyclopropylamine)$_2$I$_2$], were mixed with 10 ml of 0.67M HClO$_4$ and then there was added 30 ml of ethanol. After about 4.5 hours, a red precipitate was filtered off. The precipitate was washed with a mixture of alcohol and water 1:1 (20 ml) and then with water to yield 1.55 mm of product [Pt(cyclopropylamine)I$_2$]$_x$ (78% yield).

The [Pt(cyclopropylamine)I$_2$]$_x$ (1.55 mm) was suspended in 30 ml of water containing 5 mm of 1N ammonium hydroxide. After 3 hours of stirring, the red starting material disappeared and was replaced by a yellow solid. The mixture was stirred overnight at room temperature. The solid was then filtered off and washed with water. The reaction was quantitative. Analysis: C 16.30, H 2.28, I 48.47; found C 16.83, H 1.83, I 48.99.

EXAMPLE 7

Preparation of cis-[Pt(cyclobutylamine)(NH$_3$)I$_2$]

Cis-[Pt(cyclobutylamine)$_2$I$_2$] (2.6 mm) was mixed with 6 ml of 0.40M HClO$_4$, 20 ml of water and 30 ml of ethanol. The mixture was stirred for 1½ hours at room temperature. The solid product [Pt(cyclobutylamine)I$_2$]$_x$ was then filtered off and washed with water. This product was suspended in 10 ml of water with 6 ml of 1N ammonium hydroxide solution and allowed to stand at room temperature overnight. The solid product was filtered off and washed with water.

EXAMPLE 8

Preparation of cis-[Pt(cyclopropylamine)(NH$_2$CH$_3$)I$_2$]

[Pt(cyclopropylamine)I$_2$]$_x$ (1 mm) prepared as in Example 6, was suspended in 20 ml of water containing 2 mm of methylamine and stirred at room temperature overnight. The yellow precipitate was then filtered off and washed with water.

EXAMPLE 9

Preparation of cis-[Pt(cyclobutylamine)(NH$_3$)Cl$_2$](RF-2 and NSC 320894)

cis-[Pt(cyclobutylamine)(NH$_3$)I$_2$] was prepared according to Example 7 and reacted with silver nitrate and KCl to yield cis-[Pt(cyclobutylamine)(NH$_3$)Cl$_2$]. Analysis: calculated, C 13.4, H 3.4, N 7.91, Cl 20.06; found, C 13.90, H 3.47, N 7.89, Cl 20.02.

| Crystal structure of cis-8Pt(cyclobutylamine)(NH$_3$)Cl$_2$] (RF-2 and NSC 320894) | |
|---|---|
| Crystal Data | |
| PtCl$_2$C$_4$H$_{12}$N$_2$ | M.W. = 354.15 |
| Monoclinic, P2$_1$/c | |
| a = 8.730 Å | |
| b = 9.944 Å | |
| c = 10.082 Å | |
| β = 105.01° | |
| V = 845.4 Å$^3$ | |
| Z = 4 | |
| d = 2.782 g cm$^{-3}$ | |
| μ(MoKα) = 179.76 cm$^{-1}$ | |
| λ(MoKα) = 0.71069 Å | |

The following data relates to the atoms numbered as follows:

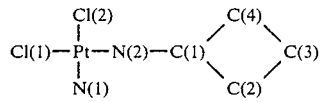

The hydrogen atoms are not shown.

TABLE 1

Positional parameters, with their e.s.d.'s and temperature factors (all × 10$^4$)

| ATOM | x | y | z | Ueq (Å$^2$)* |
|---|---|---|---|---|
| Pt | 4213.3(5) | 1115.8(5) | 971.3(5) | 264 |
| Cl(1) | 5578(4) | 580(4) | 3190(3) | 400 |
| Cl(2) | 2437(4) | −630(4) | 870(4) | 415 |
| N(1) | 5844(14) | 2619(11) | 1032(13) | 394 |
| N(2) | 3027(14) | 1637(12) | −1013(11) | 366 |
| C(1) | 1486(16) | 2246(13) | −1162(13) | 319 |
| C(2) | 498(18) | 2578(16) | −2636(14) | 441 |
| C(3) | −85(21) | 3842(17) | −2074(19) | 579 |
| C(4) | 1427(17) | 3739(15) | −785(16) | 476 |

*Ueq = ⅓ (U$_{11}$ + U$_{22}$ + U$_{33}$ + 2 U$_{13}$ cos β)

TABLE 2

Anisotropic thermal parameters ($\times 10^4$) in the form exp. $[-2\pi^2 (U_{11}h^2a^{*2} + U_{22}k^2b^{*2} + U_{33}l^2c^{*2} + 2U_{12}hka^*b^* + 2U_{13}hla^*c^* + 2U_{23}klb^*c^*)$. Standard deviations are given in parenthesis.

| ATOM  | $U_{11}$ | $U_{22}$ | $U_{33}$ | $U_{12}$ | $U_{13}$ | $U_{23}$ |
|-------|----------|----------|----------|----------|----------|----------|
| Pt    | 278(2)   | 276(2)   | 266(2)   | 47(2)    | 40(1)    | 12(2)    |
| Cl(1) | 466(19)  | 444(17)  | 315(16)  | 2(15)    | 34(14)   | 15(14)   |
| Cl(2) | 431(18)  | 405(16)  | 445(19)  | −32(15)  | 72(15)   | −1(15)   |
| N(1)  | 516(71)  | 291(54)  | 415(62)  | −88(52)  | 51(54)   | 27(48)   |
| N(2)  | 488(68)  | 388(56)  | 267(51)  | 166(54)  | 50(48)   | 36(47)   |
| C(1)  | 350(65)  | 350(63)  | 260(58)  | 17(54)   | −10(50)  | 14(50)   |
| C(2)  | 505(86)  | 548(87)  | 286(67)  | −11(72)  | −18(61)  | 51(65)   |
| C(3)  | 619(102) | 493(89)  | 638(106) | 210(88)  | −114(85) | 138(85)  |
| C(4)  | 353(68)  | 442(83)  | 541(87)  | 38(64)   | −76(61)  | −99(70)  |

TABLE 3

Bond distances and angles

| ATOM        | DISTANCE(Å) | ATOMS             | ANGLE(°)  |
|-------------|-------------|-------------------|-----------|
| Pt—Cl(1)    | 2.308(4)    | Cl(1)—Pt—Cl(2)    | 92.4(2)   |
| Pt—Cl(2)    | 2.312(4)    | Cl(1)—Pt—N(1)     | 87.7(4)   |
| Pt—N(1)     | 2.053(14)   | Cl(1)—Pt—N(2)     | 178.6(4)  |
| Pt—N(2)     | 2.067(13)   | Cl(2)—Pt—N(1)     | 177.9(4)  |
| N(2)—C(1)   | 1.46(2)     | Cl(2)—Pt—N(2)     | 89.0(4)   |
| C(1)—C(2)   | 1.54(2)     | N(1)—Pt—N(2)      | 90.9(5)   |
| C(1)—C(4)   | 1.54(2)     | Pt—N(2)—C(1)      | 115(1)    |
| C(2)—C(3)   | 1.52(3)     | N(2)—C(1)—C(2)    | 117(1)    |
| C(3)—C(4)   | 1.59(3)     | N(2)—C(1)—C(4)    | 117(1)    |
|             |             | C(1)—C(2)—C(3)    | 88(1)     |
|             |             | C(2)—C(3)—C(4)    | 88(1)     |
|             |             | C(1)—C(4)—C(3)    | 86(1)     |
|             |             | C(2)—C(1)—C(4)    | 89(1)     |

TABLE 4

Torsion angles in the cyclobutylamine ligand.
Torsion angles*

| ATOMS           | ANGLE(°) |
|-----------------|----------|
| Pt N(2) C(1) C(2) | −176.7 |
| Pt N(2) C(1) C(4) | 79.1   |
| N(2) C(1) C(2) C(3) | −142.8 |
| N(2) C(1) C(4) C(3) | 141.4 |
| C(1) C(2) C(3) C(4) | 21.5 |
| C(2) C(3) C(4) C(1) | −21.7 |
| C(3) C(4) C(1) C(2) | 21.3 |
| C(4) C(1) C(2) C(3) | −22.4 |

Calculated positions of the hydrogen atoms

| ATOM | x      | y      | z       |
|------|--------|--------|---------|
| H(1) | .3602  | .2198  | −.1318  |
| H(2) | .2915  | .0930  | −.1515  |
| H(3) | .1116  | .1578  | −.0623  |
| H(4) | −.0313 | .1926  | −.3023  |
| H(5) | .1116  | .2718  | −.3275  |
| H(6) | −.0129 | .4619  | −.2648  |
| H(7) | −.1089 | .3750  | −.1869  |
| H(8) | .2327  | .4261  | −.0868  |
| H(9) | .1233  | .3934  | .0080   |

B (isotropic) = 6.0 Å$^2$

*The conventions suggested by Sundaralingam (Biopolymers 7, 821, 1969) and Trueblood and co-workers (J. Mol. Biol. 2, 363, 1960; Acta Cryst. 18, 1067, 1965) have been used.

TABLE 5

Distances and angles between atoms possibly involved in hydrogen bonds.

| ATOMS         | TRANSLATION ON 2nd ATOM         | DISTANCE(Å) | ATOMS              | ANGLE(°) |
|---------------|----------------------------------|-------------|--------------------|----------|
| N(1)...Cl(1)  | x, ½ − y, z − ½                  | 3.34(1)     | Pt—N(1)...Cl(1)    | 118.2(6) |
| N(1)...Cl(1)  | 1 − x, ½ + y, ½ − z              | 3.36(1)     | Pt—N(1)...Cl(1)    | 110.5(5) |
| N(1)...Cl(2)  | 1 − x, − y, − z                  | 3.37(1)     | Pt—N(1)...Cl(2)    | 87.9(5)  |
| N(1)...Cl(2)  | 1 − x, ½ + y, ½ − z              | 3.55(1)     | Pt—N(1)...Cl(2)    | 121.0(5) |
| N(2)...Cl(1)  | x, ½ − y, z − ½                  | 3.54(1)     | C(1)—N(2)...Cl(1)  | 130.9(9) |
|               |                                  |             | Pt—N(2)...Cl(1)    | 106.1(5) |
| N(2)...Cl(1)  | 1 − x, − y, − z                  | 3.77(1)     | C(1)—N(2)...Cl(1)  | 105.1(9) |
|               |                                  |             | Pt—N(2)...Cl(1)    | 102.4(5) |

EXAMPLE 10

Preparation of cis-[Pt(cyclopropylamine)(ethylamine)Cl$_2$](NSC 312886)

Following the preferred general procedure, employing cis-[Pt(cyclopropylamine)$_2$I$_2$] as the starting material and adding ethylamine to the oligomer, the title compound was prepared. Analysis: calculated C 15.79, H 3.64; found C 16.31, H 3.83.

EXAMPLES 11-27

Following the preferred general procedure, the following compounds were prepared. The first recited ligand is the L ligand from the oligomer, whereas the second recited ligand was supplied by reaction with the oligomer. The last recited monodentate ligands or bidentate ligand was provided by reaction of the silver nitrate derived species IV with the appropriate anion:

| Example No. | List of compounds prepared | NSC# |
|-------------|-----------------------------|------|
| 11          | cis-[Pt(2,4-lutidine)(DMF)Cl$_2$] | 267898 |
| 12          | cis-[Pt(pyridine)(NH$_3$)Cl$_2$] | 312603 |
| 13          | cis-[Pt(NH$_2$—C$_2$H$_5$)(NH$_3$)Cl$_2$] | 312604 |
| 14          | cis-[Pt(pyridine)(cyclopropylamine)Cl$_2$] | 312605 |
| 15          | cis-[Pt(cyclopropylamine)(NH$_2$—CH$_3$)Cl$_2$] | 319969 |
| 16          | cis-[Pt(cyclopropylamine)(NH$_3$)Cl$_2$] | 319970 |
| 17 (RF-1)   | cis-[Pt(cyclopentylamine)(NH$_3$)Cl$_2$] | 323978 |

-continued

| Example No. | | NSC# |
|---|---|---|
| 18 | cis-[Pt(cyclopropylamine)(4-HOCH$_2$—pyridine)Cl$_2$] | |
| 19 | cis-[Pt(cyclopropylamine)(3-picoline)Cl$_2$] | |
| 20 | cis-[Pt(cyclopropylamine)(2-picoline)Cl$_2$] | |
| 21 | cis-[Pt(pyridine)(L-2-Aminopropanol)Cl$_2$] | |
| 22 (RF-4) | cis-[Pt(cyclobutylamine)(NH$_3$)(cis-1,2-cyclohexyldicarboxylate)] | 349460 |
| 23 (RF-5) | cis-[Pt(cyclobutylamine)(NH$_3$)(trans-1,2-cyclobutyldicarboxylate)] | |
| 24 (RF-6) | cis-[Pt(cyclobutylamine)(NH$_3$)(1,1'-cyclopentyldicarboxylate)] | |
| 25 (RF-7) | cis-[Pt(cyclobutylamine)(NH$_3$)(trans-1,2-cyclohexyldicarboxylate)] | |
| 26 (RF-8) | cis-[Pt(cyclopentylamine)(NH$_3$)(1,1'-cyclobutyldicarboxylate)] | |
| 27 | cis-[Pt(cyclopentylamine)(NH$_3$)(1,1'-cyclopentyldicarboxylate)] | |
| | Elemental Analysis | |
| 16 | calculated: C 10.56, H 2.93; found: C 10.32, H 2.94 | |
| 17 (RF-1) | calculated: C 16.30, H 3.80; found: C 16.21, H 3.95 | |
| 26 (RF-8) | calculated: C 30.07, H 4.56, N 6.38; found: C 29.36, H 4.57, N 6.56 | |
| 27 | calculated: C 39.10, H 6.22, N 4.80; found: C 37.93, H 6.03, N 4.66 | |

EXAMPLES 28–33

Following the preferred general procedure through the silver nitrate addition step, the resultant species IV was reacted with a tetradentate anionic e.g. a tetracarboxylate in a ratio of one mole of tetracarboxylate for each two moles of platinum to yield the following compounds:

| Example No. | Compound | |
|---|---|---|
| 28 (RF-11) | cis-[(Pt(cyclobutylamine)(NH$_3$))$_2$(cis, cis, cis, cis-1,2,3,4-cyclopentyltetracarboxylate)] | |
| 29 (RF-13) | cis-[(Pt(cyclobutylamine)(NH$_3$))$_2$(1,1',3,3'cyclobutyltetracarboxylate)] | |
| 30 (RF-12) | cis-[(Pt(cyclobutylamine)(NH$_3$))$_2$(benzene-1,2,4,5-tetracarboxylate)] | |
| 31 (RF-3) | cis-[(Pt(ammine)$_2$)$_2$(benzene-1,2,4,5-tetracarboxylate)] | NSC 324329 |
| 32 | cis-[(Pt(cyclopentylamine)$_2$)$_2$(benzene-1,2,4,5-tetracarboxylate)] | NSC 324330 |
| 33 | cis-[(Pt(methylamine)$_2$)$_2$(benzene-1,2,4,5-tetracarboxylate)] | NSC 324331 |

A number of the above compounds have been and/or are being evaluated by the National Cancer Institute (USA).

The data available follows:

TABLE 6

| Compound of Example No. | System Tumor[1] | Host[2] | T/C % (max.) | Concentration (mg/kg) | NCI Classification |
|---|---|---|---|---|---|
| 11 | LE | 06 | 140 | 6.25 | deferred |
| 12 | LE | 06 | 102 | 3.13 | no activity |
| 13 | LE | 06 | 134 | 3.13 | deferred |
| | LE | 02 | 157 | 3.00 | |
| 14 | LE | 06 | 143 | 3.13 | selected for further study |
| | LL | 1A | 204 | 1.51 | |
| | LL | 02 | 126 | 3.12 | |
| | PS | 02 | 192 | 12.0 | |
| | C8 | 02 | 188 | 50.0 | |
| | B1 | 02 | 152 | 6.25 | |
| | B1 | 1A | 159 | 12.5 | |
| | CD | 49 | 121 | 62.0 | |
| 10 | LE | 06 | 136 | 6.25 | deferred |
| 15 | LE | 06 | 131 | 12.5 | deferred |
| 16 | LE | 06 | 148 | 6.25 | deferred |
| 9 | LE | 06 | 200 | 3.12 | selected for further study |
| 17 | LE | 06 | 182 | 3.12 | |
| 31 | LE | 06 | 150 | 1.56 | selected for further study |
| 32 | LE | 06 | 124 | 2.00 | no activity |
| 33 | LE | 06 | 107 | 2.00 | no activity |

Tumor[1]  PS = P388 lymphocytic leukemia
LE = L1210 lymphoid leukemia
LL = Lewis lung carcinoma
C8 = Colon 38
B1 = B16 melanocarcinoma
CD = CD$_8$F$_1$ mamary tumor
Host[2] (rat or mouse strain)
06 CDF$_1$  1A B$_6$C$_3$F$_1$

TABLE 6-continued

| Compound of Example No. | System Tumor[1] | Host[2] | T/C % (max.) | Concentration (mg/kg) | NCI Classification |
|---|---|---|---|---|---|
| | 02 BDF$_1$ | 49 CD$_8$F$_1$ | | | |

TABLE 7

Summary of Anti-L1210 Activities

| Compound of Example No. | Max. % T/C - Cures/total (O.D. mg/kg/inj) | |
|---|---|---|
| | Day 1 | QD 1→9 (1→5) |
| 18 (RF-1) | (a)215(8) | 200(1) |
| | (b)242(8) | |
| 17 (RF-2) | (a)223(8) | 246(2) |
| | (b)250(8) | |
| 31 (RF-3) | (a)162(16) | 192(4) |
| | (b)150(16) | |
| 23 (RF-4) | (a)183(64) | 183(16) |
| | (b) | |
| 24 (RF-5) | (a)150(64) | (a)175(16) |
| | (b) | (b) |
| 25 (RF-6) | 106(64) | 113(16) |
| 26 (RF-7) | (a)144(64) | (a)188(16) |
| | (b) | (b) |
| 27 (RF-8) | 138(64) | 138(16) |
| 28 (RF-11) | (a)150(32) | (a)175(16) |
| | (b) | (b) |
| 30 (RF-12) | (a)156(64) | (a)156(16) |
| | (b) | (b) |

TABLE 8

Effect of Platinum Compounds on B16 Melanoma

| Material | Dose, IP mg/kg/inj | MST Days | Effect MST % T/C | AWC, d.6 | Survivors Day 10(60) |
|---|---|---|---|---|---|
| Cis-DDP | 2.4 | 42.0 | 210 | −4.5 | 10/10(1) |
| | 1.6 | 42.0 | 210 | −2.6 | 9/9(1) |
| | 0.8 | 30.5 | 153 | −1.2 | 10/10 |
| Ex. 17 | 4 | Tox | Tox | −4.2 | 1/10 |
| | 3 | Tox | Tox | −3.8 | 2/10 |
| | 2 | 20.5 | 103 | −2.9 | 10/10 |
| | 1 | 38.5 | 193 | −2.3 | 10/10 |
| | 0.5 | 37.0 | 185 | −1.4 | 10/10 |
| Ex. 9 | 4 | Tox | Tox | −5.3 | 0/10 |
| | 3 | 12.0 | 60 | −4.3 | 7/10 |

TABLE 8-continued

Effect of Platinum Compounds on B16 Melanoma

| Material | Dose, IP mg/kg/inj | MST Days | Effect MST % T/C | AWC, d.6 | Survivors Day 10(60) |
|---|---|---|---|---|---|
| | 2 | 36.5 | 183 | −3.2 | 10/10 |
| | 1 | 32.0 | 160 | −2.2 | 10/10 |
| | 0.5 | 29.0 | 145 | −2.1 | 9/9 |
| Ex 31 | 6 | Tox | Tox | −5.4 | 1/10 |
| | 4 | Tox | Tox | −5.0 | 4/10 |
| | 2 | 32.5 | 163 | −3.1 | 10/10 |
| | 1 | 30.0 | 150 | −2.2 | 8/9 |
| Control | Saline | 20.0 | — | −1.3 | 10/10 |

Tumor inoculum: 0–5 ml of a 10% tumor brei, ip.
Host: TBDF$_1$ ♂ mice
Tox: <7/10 mice alive on d. 10.
Treatment: QD 1→9.
Evaluation: MST = median survival time.
Effect: % T/C = (MST treated/MST control) × 100.
Criteria: % T/C ≧ 125 considered significant antitumor activity A number of the various cis-[PtLL′X$_2$] or [PtLL′Y] compounds disclosed herein have shown at least some anti-tumor activity. Much is yet to be learned about the in vivo activity of various platinum (II) compounds. To date, the cis-Pt(II) compounds rather than trans-Pt(II) compounds appear to be preferred for anti-tumor activity. The process of the invention and the various intermediates and resultant cis-Pt(II) compounds are useful in aiding researchers in understanding in vivo activity of Pt(II) compounds and in the possible development of new anti-tumor compounds.

TABLE 9

INFRARED DATA

[Pt(cyclopropylamine)I$_2$]$_x$
3212(s), 3175(s), 3106(m), 1566(s), 1415(w), 1250(m), 1220(m), 1197(m), 1098(w), 1080(w), 1049(w), 1023(s), 824(s), 817(m), 753(m), 708(w), and 382(m) cm$^{-1}$.

[Pt(cyclobutylamine)I$_2$]$_x$
3230(m), 3160(s), 3080(m), 1545(s), 1238(w), 1212(m), 1175(m), 1137(m), 1064(s), 927(m), 870(m), 762(w), 740(w), 708(m) and 606(m) cm$^{-1}$.

Example 6: cis-[Pt(cyclopropylamine)(NH$_3$)I$_2$]
3280(m), 3228(s), 3172(s), 3090(m), 1545(s), 1242(s), 1198(s), 1180(s), 1026(m), 1047(m), 1012(s), 910(w), 816(m), 807(m), 758(m), 671(s), 473(w), 374(m).

Example 8: cis-[Pt(cyclopropylamine)NH$_2$—CH$_3$)I$_2$]
3200(br), 1582(s), 1560(w), 1421(m), 1409(m), 1256(m), 1193(s), 1070(m), 1016(m), 998(w), 918(w), 820(s), 752(m), 725(w), 565(w), 478(w), 386(w).

Example 9: cis-[Pt(cyclobutylamine)(NH$_3$)Cl$_2$]
3280(s), 3258(s), 3212(s), 1545(m), 1525(m), 1300(s), 1226(w), 1198(s), 1136(s), 1075(s), 1000(w), 940(m), 933(m), 885(w), 810(m), 792(m), 758(w), 712(m), 618(w), 572(w), 506(w), 400(m), 320(s).

cis-[Pt(isopropylamine)(NH$_3$Cl$_2$]
3250(s), 3205(s), 3130(w), 1578(s), 1555(m), 1300(w), 1236(m), 1143(m), 1095(w), 1055(w), 925(m), 800(w), 746(w), 607(w), 423(w) and 310(s) cm$^{-1}$.

Example 15: cis-[Pt(cyclopropylamine)NH$_2$CH$_3$)Cl$_2$]
3260(s), 3230(s), 3200(s), 1580(w), 1399(m), 1301(w), 1262(m), 1242(m), 1224(m), 1188(m), 1097(w), 1069(s), 1010(s), 981(w), 915(w), 807(s), 744(w), 734(s), 708(w), 380(w), 312(s) and 308(s) cm$^{-1}$.

Example 16: cis[Pt(cyclopropylamine)(NH$_3$)Cl$_2$]
3276(s), 3226(s), 3187(s), 1642(w), 1580(w), 1575(m), 1537(m), 1390(w), 1300(w), 1265(w), TABLE 9-continued

INFRARED DATA

1232(m), 1200(m), 1160(w), 1115(w), 1090(m), 1040(w), 1022(m), 1015(m), 956(w), 930(w), 815(s), 786(s), 750(w), 722(s), 590(w), 515(w), 392(m), 328(s), 316(s).

Example 31: cis-[Pt(NH$_3$)$_2$)$_2$ (benzene-1,2,4,5-tetracarboxylate)]
$\nu$(C = 0): 1550 cm$^{-1}$, other strong bands: 1130, 860, 810, 760, 427 and 372 cm$^{-1}$.

(s = strong, m = medium, w = weak, br = broad, (measured in Nujol))

We claim:

1. A method for the preparation of an oligomer having the empirical formula [PtLI$_2$]$_x$ where x is a lower integer, 2 or higher and each L is the same and is ammine, a primary or secondary mono amine or a pyridine-type amine, coordinated to the Pt through the amine nitrogen, or dimethylformamide coordinated through the oxygen atom to the platinum which method comprises reacting a compound corresponding to the formula cis-[PtL$_2$I$_2$]

where L is as defined above in the presence of a molar excess of a platinum non-reactive aqueous acid in admixture with a water miscible inert solvent for said [PtL$_2$I$_2$], thereby forming said oligomer.

2. The method as in claim 1 where L is a primary or secondary monoamine or a pyridine-type amine.

3. The method as in claims 1 or 2 where the solvent is a lower alkanol.

4. The method as in claim 3 where the acid is perchloric acid.

5. An oligomer corresponding to the emperical formula

[PtLI$_2$]$_x$ where x is a lower integer, 2 or higher, and each L is the same and is ammine, a primary or secondary mono amine or a pyridine-type amine.

6. The oligomer as in claim 5 where L is a primary or secondary monoamine or a pyridine-type amine.

7. A method for the preparation of a platinous complex corresponding to the formula cis-[PtLL′I$_2$]

where L≠L′ and where L and L′ is ammine, a primary or secondary monoamine, a pyridine-type amine, or N,N-dimethylformamide which comprises reacting an oligomer corresponding to the formula

[PtLI$_2$]$_x$ where x is a lower integer, 2 or higher, with an amine or N,N-dimethylformamide (L′), in a reaction medium in which the product is substantially insoluble comprising, essentially in water, to form said cis-[PtLL′I$_2$].

8. The method as in claim 7 where L is a primary or secondary monoamine or a pyridine type amine.

9. The method as in claims 7 or 8 where the reaction medium is water.

10. An oligomer as in claim 5 wherein each L is the same and is ammine, or a primary or secondary mono amine.

* * * * *